United States Patent
Lindsay et al.

[11] Patent Number: 6,105,912
[45] Date of Patent: Aug. 22, 2000

[54] RESERVOIR MOUNTING BRACKET

[75] Inventors: Erin J. Lindsay, Manchester; Daniel W. Viitala, Dexter, both of Mich.

[73] Assignee: Terumo Cardiovascular Systems Corporation, Somerset, N.J.

[21] Appl. No.: 08/966,399

[22] Filed: Nov. 7, 1997

[51] Int. Cl.⁷ .............................. A47K 1/00; A61B 19/00; A61M 1/00
[52] U.S. Cl. ...................... 248/223.41; 604/403; 604/322
[58] Field of Search ............................ 248/283.1, 229.15, 248/229.25, 282.1, 231.71, 285.1, 295.11, 296.1, 469, 309.1, 223.41; 211/98, 41.17, 41.12, 26, 40; 604/4, 5, 6

[56] References Cited

U.S. PATENT DOCUMENTS

| | | | |
|---|---|---|---|
| 3,734,351 | 5/1973 | Gaudin | 222/103 |
| 3,992,706 | 11/1976 | Tunney et al. | 340/239 |
| 4,019,656 | 4/1977 | Spears | 222/103 |
| 4,019,707 | 4/1977 | Quinn et al. | 248/95 |
| 4,085,866 | 4/1978 | Fekl | 222/158 |
| 4,187,845 | 2/1980 | Dror | 128/205 |
| 4,295,619 | 10/1981 | Kulin et al. | 248/95 |
| 4,393,880 | 7/1983 | Taylor | 128/760 |
| 4,449,969 | 5/1984 | Schweizer | 604/322 |
| 4,500,308 | 2/1985 | Kurtz et al. | 604/4 |
| 4,717,377 | 1/1988 | Fukasawa | 604/4 |
| 4,863,452 | 9/1989 | Irmiter et al. | 604/408 |
| 4,976,707 | 12/1990 | Bodicky et al. | 604/408 |
| 5,049,146 | 9/1991 | Bringham et al. | 604/4 |
| 5,352,218 | 10/1994 | Buckley et al. | 604/407 |
| 5,573,526 | 11/1996 | Hess | 604/408 |
| 5,693,039 | 12/1997 | Stewart et al. | 604/407 |
| 5,720,741 | 2/1998 | Stewart et al. | 604/407 |
| 5,820,086 | 10/1998 | Hoftman et al. | 248/295.11 |

FOREIGN PATENT DOCUMENTS

| | | |
|---|---|---|
| 0 080 610 B1 | 2/1986 | European Pat. Off. . |
| 0 401 016 A1 | 12/1990 | European Pat. Off. . |
| 0 348 682 B1 | 8/1992 | European Pat. Off. . |
| 0 401 016 B1 | 4/1994 | European Pat. Off. . |
| WO 86/02825 | 5/1986 | WIPO . |
| WO 95/07725 | 3/1995 | WIPO . |
| WO 96/35462 | 11/1996 | WIPO . |

*Primary Examiner*—Anita M. King
*Assistant Examiner*—Michael Nornberg
*Attorney, Agent, or Firm*—Burns, Doane, Swecker & Mathis, LLP

[57] ABSTRACT

A blood reservoir mounting bracket supports alternate sizes of blood reservoir assemblies. The reservoir mounting bracket has a reversible reservoir mounting frame, with mounting pins on one side thereof arranged in a first pattern for the mounting holes of one size of a blood reservoir assembly, and mounting pins on its other side arranged in a second pattern for the mounting holes of a second, different sized blood reservoir assembly. Alternatively, the reservoir mounting bracket has a reservoir mounting frame with retractable pins therein for use in adapting to differently arrayed holes on different sized blood reservoir assemblies. The reservoir mounting bracket further has an oxygenator holder which allows orientation of the oxygenator in a plurality of positions.

19 Claims, 9 Drawing Sheets

RESERVOIR MOUNTING BRACKET

BACKGROUND OF THE INVENTION

The present invention relates to venous reservoir holder assemblies, and more specifically to a reservoir mounting bracket for use in containing venous blood during cardiopulmonary bypass surgery.

A cardiopulmonary bypass is a surgical technique for diverting a patient's blood around the heart and lungs. The blood flow is directed away from the patient at the entrance to the right atrium of the heart, conditioned by mechanical means and then recirculated into the patient at the aorta. By circulating the extracorporeal blood through an oxygenator, an apparatus for introducing oxygen into the blood during extracorporeal circulation, the oxygenated blood can be recirculated in vivo.

As heart surgery employing extracorporeal circulation has become more widely accepted, the demand for the products required to perform such procedures has grown rapidly. Thus, numerous arrangements have been proposed for supporting and manipulating the venous blood during in vitro oxygenation. Such arrangements include various collapsible and expandable containers working under the influence of a vacuum and in conjunction with movable rigid plates.

One such venous reservoir bag support assembly is the Cobe Closed Venous Reservoir Bag, commercially available from Cobe Cardiovascular, Inc. in Arvada, Colo., and disclosed in UK Patent Application GB 2 245 176 A. The Cobe reservoir bag support assembly comprises a venous reservoir bag assembly mounted in a support assembly. The venous reservoir bag assembly has a plate with the venous reservoir bag being carried by the plate. The support assembly has a back plate and a front plate, the two plates being movable relative to each other.

The bag assembly is mounted with its plate in facing relation with one of the back and front plates so that the bag is located between its plate and the other plate. The Cobe Closed Venous Reservoir Bag is limited in that it supports a single reservoir bag size, leading to inefficiencies because blood reservoirs function most effectively when filled. Further, the Cobe Closed Venous Reservoir Bag requires that an oxygenator be separately mounted in the vicinity of the reservoir bag.

Another reservoir bag support system is disclosed in U.S. Pat. No. 4,943,288. This system includes a flexible bag having an external frame with locking elements to retain the bag in an extended position when the bag is being filled, with the locking elements being displaceable to permit the bag to collapse during the reinfusion process. The prior art also discloses alternative arrangements for supporting reservoir bags externally, such as U.S. Pat. Nos. 4,573,992 and 4,466,888.

Prior reservoir bag support systems have proved to be relatively inflexible. First, prior systems support only a single size reservoir bag. Because handling characteristics of the venous reservoir improve with increased reservoir volume, the reservoir functions most effectively when full. Thus, selecting the appropriate size venous reservoir for a patient's needs is critical. Prior art systems do not always allow proper reservoir selection as they only support a single reservoir size. Additionally, prior systems do not support both flexible and rigid blood reservoirs. Further, prior systems require that the blood reservoir be mounted to the support system at the point of use, namely in the operating area. Finally, prior systems require that the oxygenator be mounted separately from the reservoir bag support system in a limited number of positions. These limitations have resulted in prior blood reservoirs support systems that are expensive, difficult to handle and inconvenient and complicated to operate.

BRIEF SUMMARY OF THE INVENTION

The present invention is an improved mounting bracket for blood reservoirs. The inventive reservoir mounting bracket is versatile in that it can assume a number of positions relative to a fixed structural base on which it is mounted, and it can accept a variety of sizes of blood reservoirs. Further, the blood reservoirs can be premounted on a reservoir mounting frame, which can then be secured to the reservoir mounting bracket (which can also support an oxygenator in various orientations).

The inventive reservoir mounting bracket is mountable on an upstanding pole, and includes a mount and a reservoir mounting frame. The mount has a base member, a pair of spaced-apart frame supports extending upwardly from the base member and a support arm for selectively connecting the base member to the pole. The frame supports have opposed, facing and parallel upstanding channels therein. The reservoir mounting frame has a first major face and a second opposite major face, with opposite parallel side edges therebetween. The side edges of the reservoir mounting frame are slidably received within the facing channels of the frame supports on the mount to allow removable mounting of the frame on the mount.

In the preferred embodiment, the mount has a reservoir presentation side, and the reservoir mounting frame is movable between a first position adapted for supporting a first blood reservoir assembly when its first face is facing the reservoir presentation side of the mount, and a second position adapted for supporting a second, larger blood reservoir assembly when its second face is facing the reservoir presentation side of the mount.

The blood reservoir assembly has a plurality of mounting holes therein, with the holes of the first reservoir assembly arrayed in a first pattern and the holes of the second reservoir assembly arrayed in a second, different pattern. In one embodiment, the reservoir mounting frame has a first plurality of mounting pins on its first face which correspond to the pattern of mounting holes on the first reservoir assembly, and a second plurality of mounting pins on its second face which correspond to the pattern of mounting holes on the second reservoir assembly. In an alternative embodiment, a plurality of retractable mounting pins are disposed on the first face of the reservoir mounting frame, with a first set of those pins being disposed to correspond to the first pattern of mounting holes on the first reservoir assembly, and a second set of those pins being disposed to correspond to the second pattern of mounting holes on the second reservoir assembly.

BRIEF DESCRIPTION OF THE DRAWINGS

The present invention will be further explained with reference to the drawing figures listed below wherein like structure is referred to by like numerals throughout the several views.

While the above-identified drawings features set forth several preferred embodiments, other embodiments of the present invention are also contemplated, as noted in the discussion. This disclosure presents illustrative embodiments of the present invention by way of representation and not limitation. Numerous other modifications and embodiments can be devised by those skilled in the art which fall within the scope and spirit of the principles of this invention.

DETAILED DESCRIPTION OF THE PREFERRED EMBODIMENTS

Figure 1:
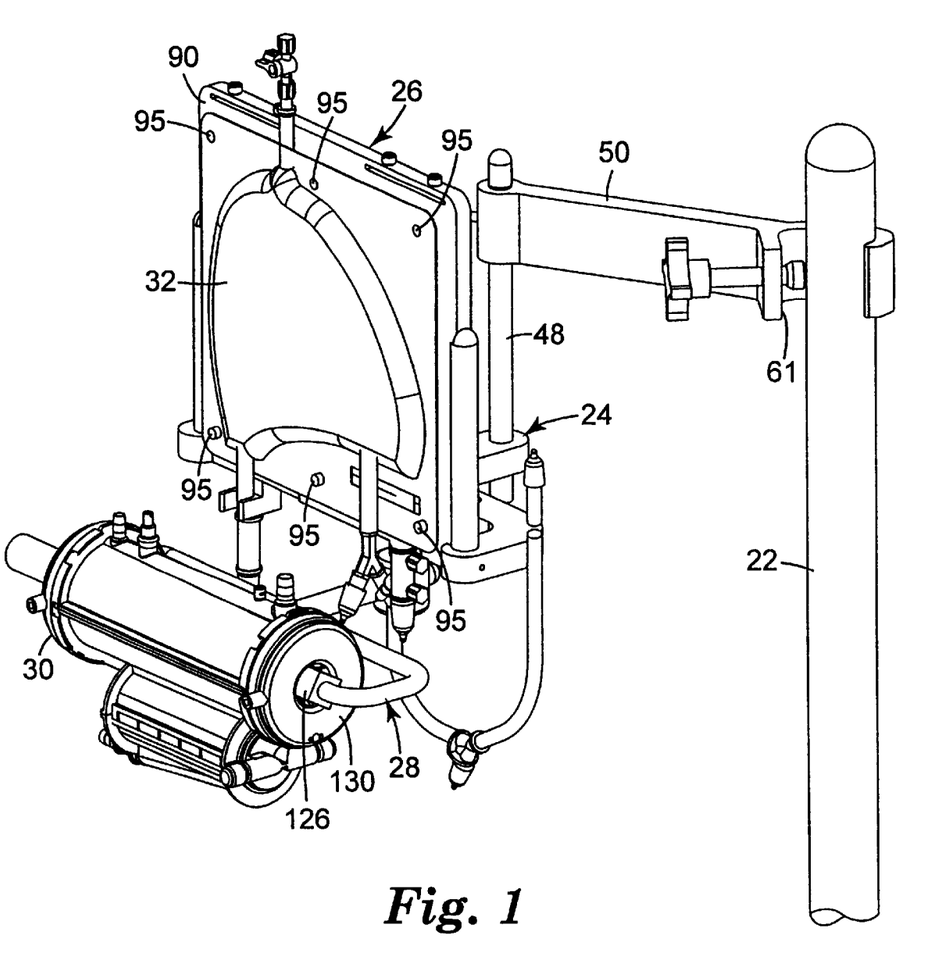
FIG. 1 is a perspective view of the reservoir mounting bracket of the present invention, shown with a flexible venous reservoir assembly and an oxygenator mounted thereon.

A reservoir mounting bracket 20 of the present invention is shown generally in FIG. 1. The reservoir mounting bracket 20 attaches to an upstanding pole 22 and includes a mount assembly 24, a frame assembly 26 and an oxygenator holder assembly 28. The frame assembly 26 supports a blood reservoir assembly 32, and the oxygenator holder assembly 28 supports an oxygenator 30.

Figure 2:
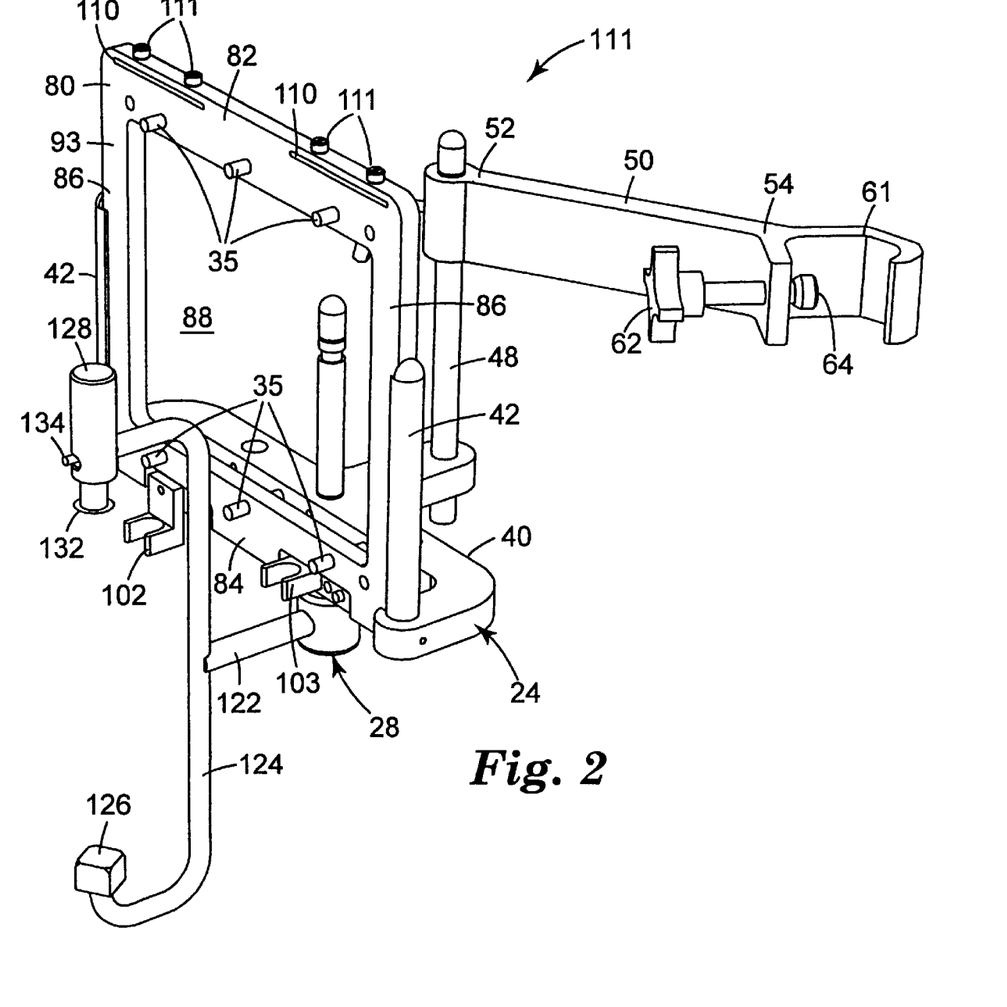
FIG. 2 is a perspective view of the reservoir mounting bracket of the present invention, shown with a reservoir mounting frame in a first position where a reservoir presentation side will support a first blood reservoir assembly.
Figure 3:
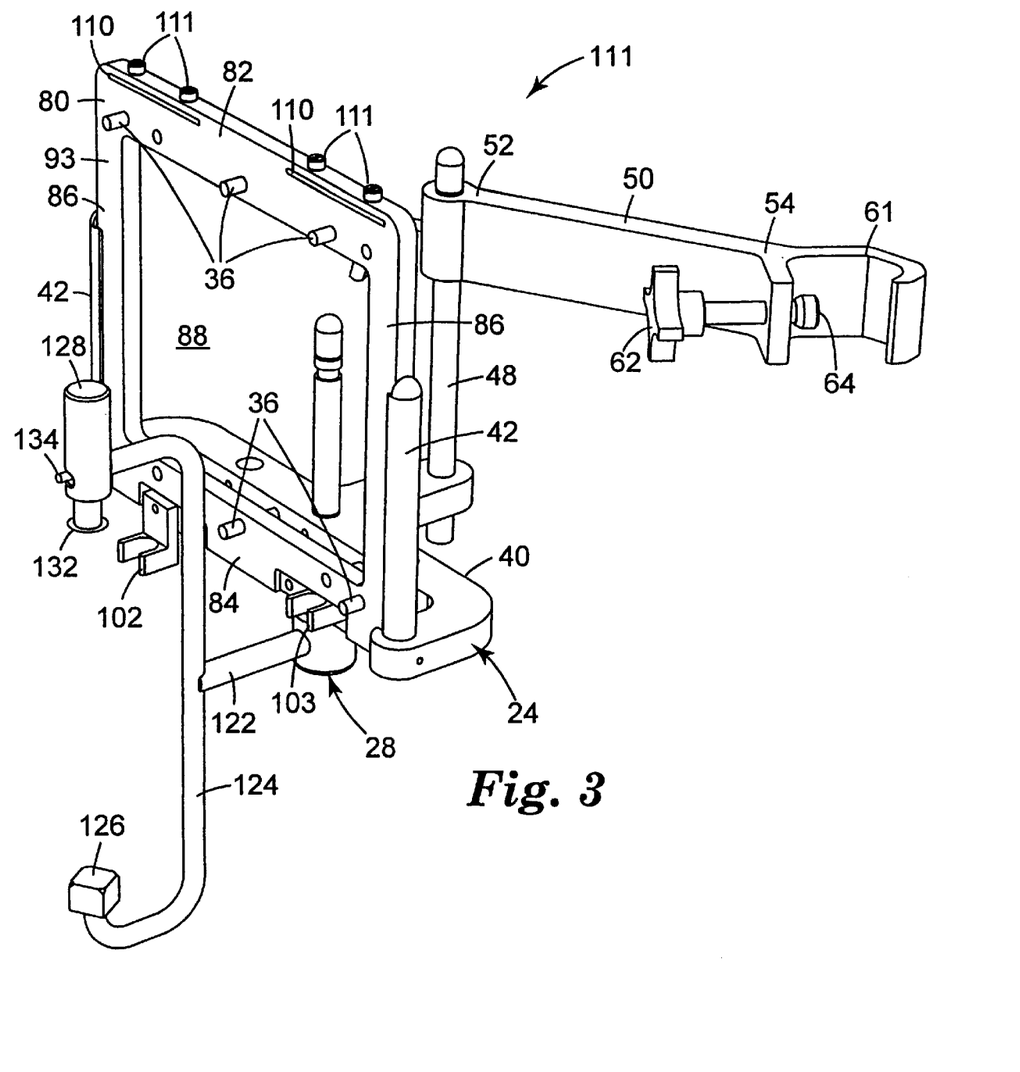
FIG. 3 is a perspective view of the reservoir mounting bracket of the present invention, shown with the reservoir mounting frame in a second position where the reservoir presentation side will support a second, larger blood reservoir assembly.

Different surgical procedures and patient needs cause a wide range of patient blood volume requirements. Because blood reservoirs function most effectively when full, the ability to support various sized blood reservoirs is an innovative and useful feature of the reservoir mounting bracket 20. The inventive reservoir mounting bracket 20 can present different mounting pin patterns for use in supporting different sizes or types of blood reservoirs. FIG. 2 illustrates a reservoir presentation side (facing the reader's left) of the frame assembly 26 adapted to support a first blood reservoir assembly on mounting pins 35. FIG. 3 shows the frame assembly 26 with its reservoir presentation side adapted to support a second, larger blood reservoir assembly on mounting pins 36. Alternative means for presenting these various embodiments are contemplated, and several such embodiments are disclosed herein.

Figure 4:
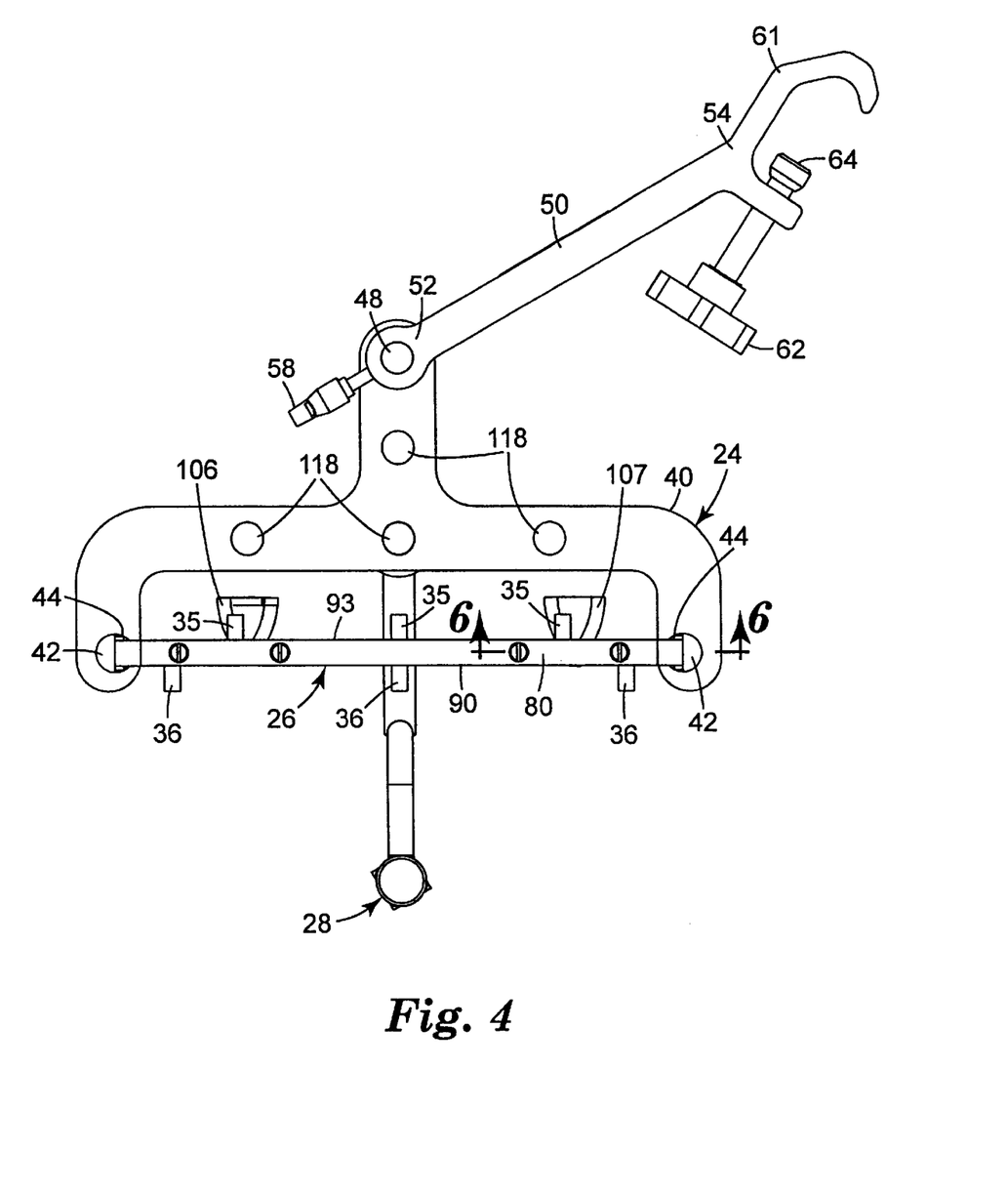
FIG. 4 is a top plan view of the reservoir mounting bracket of the present invention, as shown in FIG. 3.

The mount assembly 24 consists of a base member 40, a pair of frame supports 42, a post 48 and a support arm 50. The base member 40 is generally a Y-shaped bracket. The frame supports 42 extend upwardly from the outer branches of the Y-shaped base member 40, and have facing and parallel channels 44 therein (see FIGS. 4 and 5). The channels 44 are preferably aligned to extend vertically upward from the base member 40. The post 48 extends upwardly from the base of the Y-shaped bracket (base member 40). The support arm 50 has a first end 52 and a second end 54, with the first end 52 including a bore 56 sized to slidably and rotatably receive the post 48 therein. A threaded pivot lock 58 is provided to secure the post 48 to the support arm 50, and is adjustable for relative rotary and vertical positions of the support arm 50 with respect to the base member 40 (along the post 48). The second end 54 of the support arm 50 includes a C-clamp 61 which is designed to surround the upstanding pole 22. Tightening a threaded clamp knob 62 on the C-clamp 61 causes a pole interface 64 to come in contact with the upstanding pole 22 and secures the reservoir mounting bracket 20 to the upstanding pole 22 (and allows for rotation and vertical adjustability). The reservoir mounting bracket 20 of the present invention is thus mountable to a base structure (e.g., the pole 22) and can assume a variety of orientations relative to the base structure, by means of manipulating the C-clamp 61 or the pivot lock 58.

Figure 5:
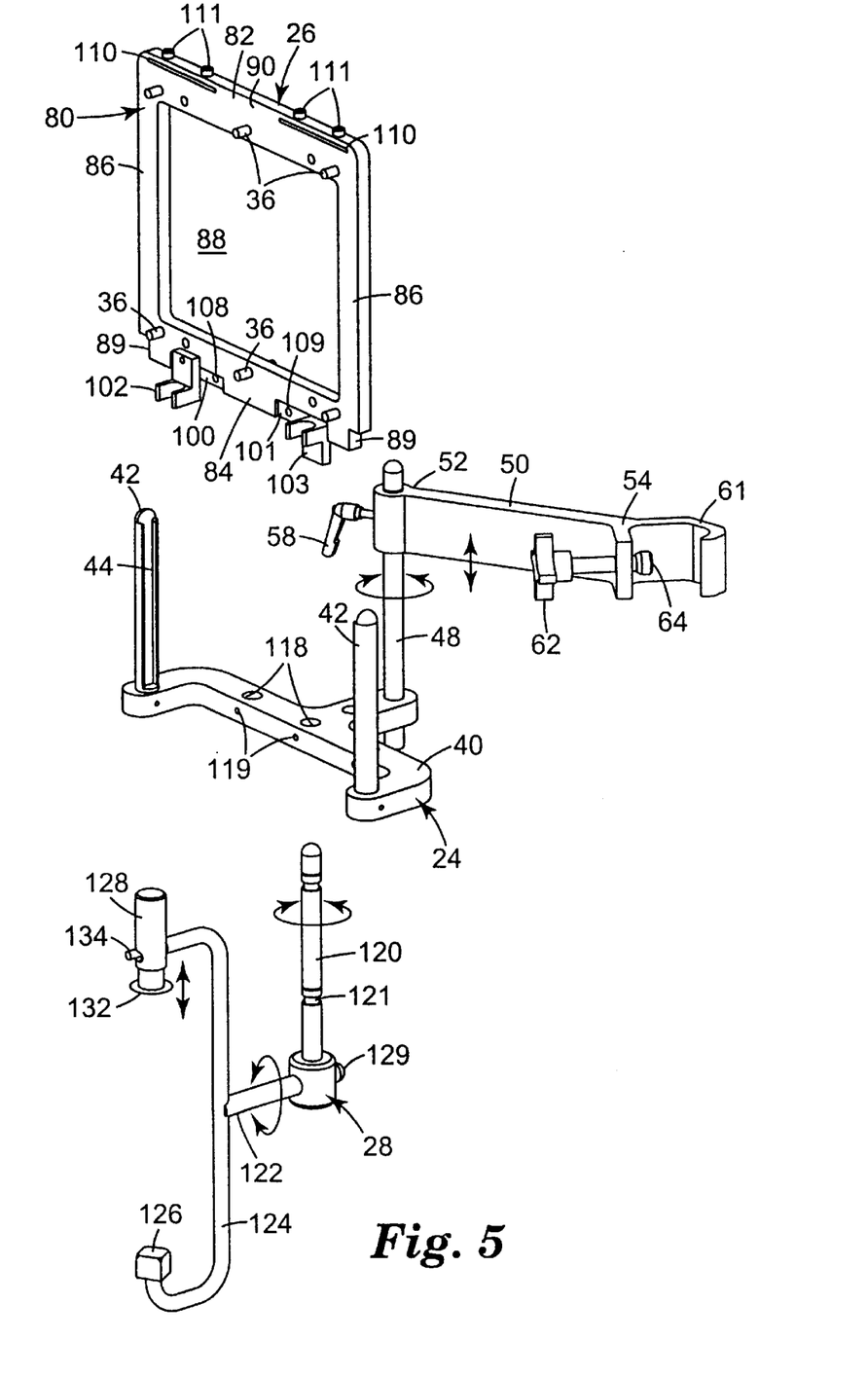
FIG. 5 is an exploded assembly view of the reservoir mounting bracket of the present invention.

As illustrated in FIG. 5, the frame assembly 26 is generally rectangular in shape and defined as a reservoir mounting frame 80 having a top edge 82, a bottom edge 84, two parallel side edges 86 and an inner opening 88. Preferably, the reservoir mounting frame 80 is formed from acetal plastic, sold under the tradename "Delrin" and available from du Pont de Nemours & Company, Inc. in Wilmington, Del. The reservoir mounting frame 80 is separable from the mount assembly 24. This allows the reservoir mounting frame 80 to be removed from the upright frame supports 42 on the base member 40 of the mount assembly 24 (to either mount or remove a blood reservoir assembly thereon or clean the reservoir mounting frame 80) and to be replaced in the frame supports 42. Thus, the frame assembly 26 can be disengaged from the mount assembly 24 to mount a blood reservoir thereon, and various sizes of flexible blood reservoirs may be mounted on the reservoir mounting frame 80 (which is then slidably mountable in the frame supports 42 of the mount assembly 24). The parallel side edges 86 of the reservoir mounting frame 80 slidably fit into the opposed channels 44 of the frame supports 42. Notched corners 89 at the juncture of each side edge 86 and the bottom edge 84 seat the reservoir mounting frame 80 in place on the base member 40 and in the channels 44.

Figure 6:
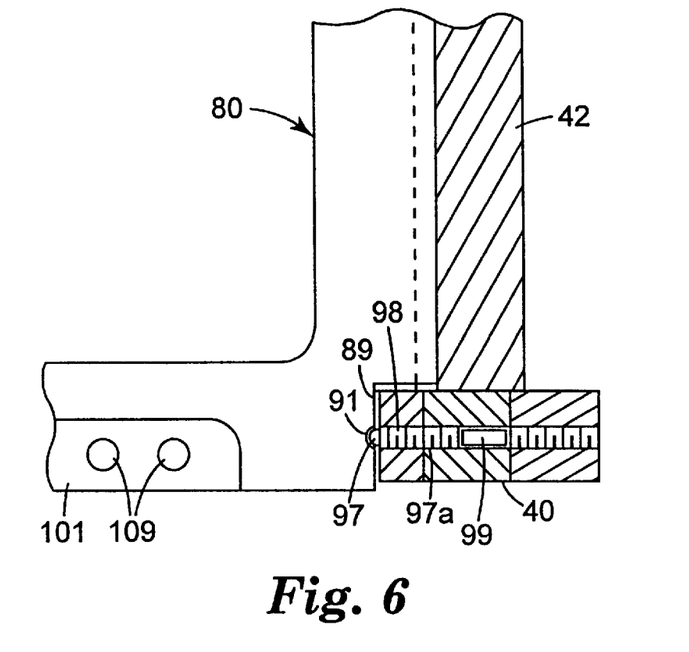
FIG. 6 is a sectional view of an interface between a mount assembly and the reservoir mounting frame of the reservoir mounting bracket of the present invention as seen from a line 6—6 in FIG. 4.

As illustrated in FIG. 6, each of the notched corners 89 feature a recessed dimple 91 that permits the reservoir mounting frame 80 to snap into place when properly positioned in the opposed channels 44 of the frame support 42. A detent ball 97 protrudes out of a bore 97a in the base member 40 by a ball plunger 98 in the bore 97a. The detent ball 97 engages the recessed dimple 91 when the reservoir mounting frame 80 is completely slid into the channels 44. A set screw pin 99 ensures the proper engagement of the recessed dimple 91 and the detent ball 97. By snapping into place, the reservoir mounting frame 80 provides the user with an audible and tactile signal that the reservoir mounting frame 80 is affirmatively secured in the opposed channels 44.

In one embodiment, the reservoir mounting frame 80 is also reversible in position relative to the mount assembly 24 and its channels 44. When mounted with a first face 90 thereof facing out (towards the reservoir presentation side (e.g., away from the pole 22)), the mounting frame 80 may support a first blood reservoir assembly such as a blood reservoir assembly 92 in FIGS. 1 and 9. When mounted with a second face 93 thereof facing out, the mounting frame 80 may support a second blood reservoir assembly such as a blood reservoir assembly 94 in FIG. 10. The mounting pins 36 on the first face 90 of the mounting frame 80 are arranged to correspond to a pattern of mounting holes 95 in the blood reservoir assembly 92 (compare FIGS. 1 and 3). The mounting pins 35 on the second face 93 are arranged to correspond to a different pattern of mounting holes 96 in the blood reservoir assembly 94 (compare FIGS. 2 and 10). The mounting pins 36 on the first face 90 protrude horizontally from the reservoir frame 80 and fit through the mounting holes 95 in designated locations on the flexible blood reservoir assembly 92, thereby defining a friction fit of the blood reservoir assembly 92 to the reservoir mounting frame 80. Likewise, the mounting pins 35 on the second face 93 protrude horizontally from the reservoir frame 80 and fit through the mounting holes 96 in designated locations on the flexible blood reservoir assembly 94, thereby defining a friction fit of the blood reservoir assembly 94 to the reservoir mounting frame 80. The reservoir mounting frame 80 must be removed and reversed in the channels 44 of the frame supports 42 to convert the reservoir mounting bracket 20 from one size blood reservoir assembly to another.

The bottom edge 84 of reservoir mounting frame 80 features recessed areas 100 and 101 where inlet and outlet port supports 102 and 103 are mounted to the reservoir mounting frame 80. The inlet and outlet port supports 102 and 103 are adjustable for use with both small and large blood reservoirs, with either a left-hand or a right-hand venous inlet. Plastic thumb screws 106 and 107 (FIG. 4) secure the inlet and outlet port supports 102 and 103 to the reservoir mounting frame 80, and a plurality of holes 108 and 109 are provided to allow alternative positioning of the port supports 102 and 103 on the mounting frame 80. The port supports 102 and 103 are mounted on the reservoir presentation side of the reservoir mounting frame 80 and aligned for clipping onto and supporting blood reservoir assembly flow lines and couplings. Thus, when removing the mounting frame 80 from the frame supports 42 and reversing its orientation, the port supports 102 and 103 must be remounted on the reservoir mounting frame 80.

A plurality of mounting slots 110 is provided along the top edge 82 of the mounting frame 80 and designed for the retention of sampling manifolds (not shown) therein. The sampling manifolds are detachable for convenient blood sampling of arterial and venous blood from the sampling ports. Securing screws 111 are provided along the top edge 82 for securing the sampling manifolds to the reservoir mounting frame 80. The sampling manifold may be inserted in either mounting slot 110, allowing greater flexibility and versatility in use of the reservoir mounting bracket 20.

In an alternative embodiment, the reservoir mounting frame 80 has no inner opening 88, but rather includes a backplate (filling the hole that was defined by the inner opening 88). The backplate is preferably formed from a transparent material, such as clear polycarbonate, permitting the blood level in the blood reservoir supported by the reservoir mounting frame to be visible from in front of or behind the reservoir mounting frame. By allowing blood volume visualization from anywhere around the blood reservoir, the solid frame embodiment enhances user convenience.

Figure 7:
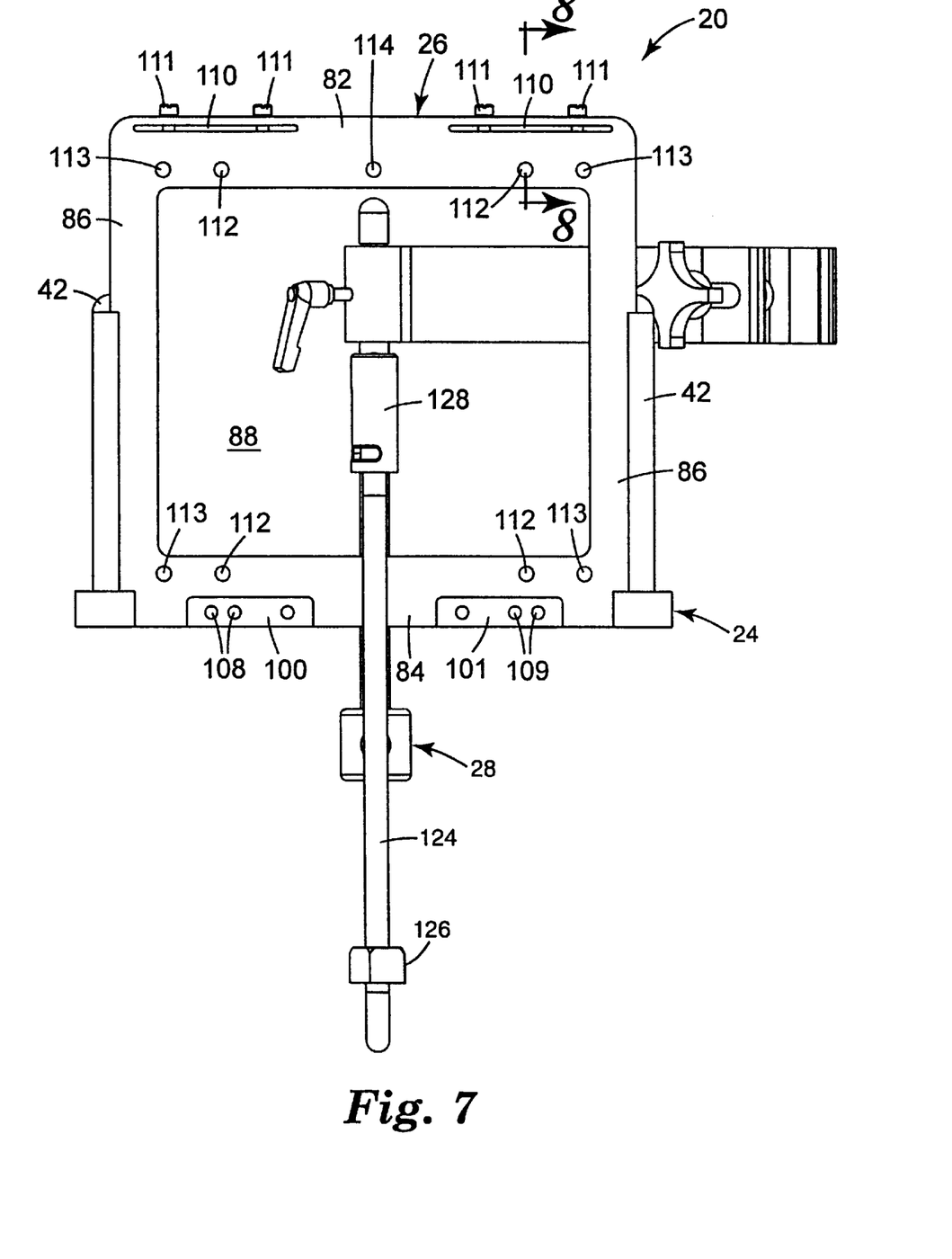
FIG. 7 is a front elevational view of the reservoir mounting bracket of the present invention, shown with the reservoir mounting frame having a plurality of retractable mounting pins.

In another alternative embodiment (FIGS. 7 and 8), the reservoir mounting frame 80 has a plurality of retractable mounting pins 112 that can serve to support either a small or large flexible blood reservoir assembly without the need for removing and reversing the reservoir mounting frame 80. The outer pins 113 and the center pins 114 on both the top edge 82 and the bottom edge 84 of the reservoir mounting frame 80 are in fixed positions (i.e., always protruding). The outer pins 113 and the center pins 114 are arranged to support the larger blood reservoir assembly 92. The retractable mounting pins 112 secure the smaller blood reservoir assembly 94 to the mounting frame 80 and retract when the larger blood reservoir assembly 92 is mounted on the mounting frame 80. The retractable mounting pins 112 move in and out of the reservoir mounting frame 80, and when retracted, do not interfere with the mounting of the larger blood reservoir assembly 92. When the smaller blood reservoir assembly 94 is mounted on the mounting frame 80, the retractable mounting pins 112 are pushed outward to assume their mounting position.

Figure 8:
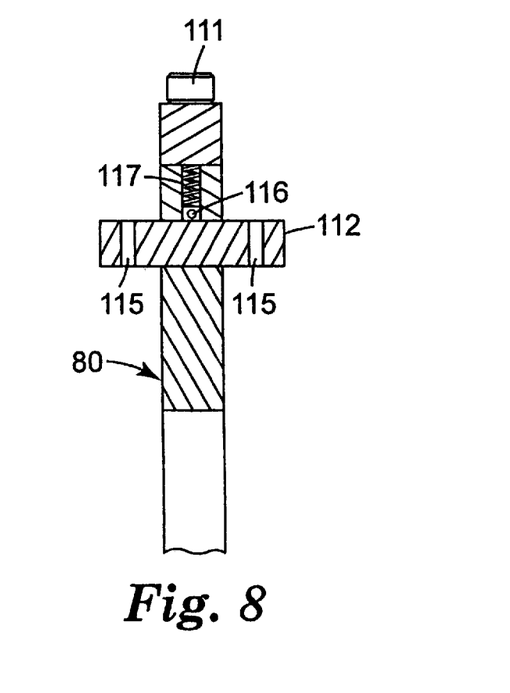
FIG. 8 is a sectional view of the reservoir mounting frame with a plurality of retractable mounting pins as seen from a line 8—8 in FIG. 7.

As shown in FIG. 8, each retractable mounting pin 112 is formed to provide depressions or holes 115 therein which cooperate with a detent 116 urged downwardly by a spring 117 retained in the reservoir mounting frame 80 to secure the retractable mounting pin 112 in its desired position. In this embodiment, reservoir mounting frame 80 has the inner opening 88 and does not need to be reversed in the frame supports 42 to mount a different size reservoir assembly therein—the retractable mounting pins 112 allow the mounting of both reservoir assemblies from the same side of the mounting frame 80. However, the reservoir mounting frame 80 may still be oriented with either its first face 90 or its second face 93 on the reservoir presentation side of the mount assembly 24.

In another alternative embodiment of the present invention, the reservoir mounting frame 80 includes the retractable mounting pins 112 with a solid frame and no inner opening 88. Instead, a backplate covers the inner opening 88. Again, the backplate is preferably formed from a transparent material, such as clear polycarbonate, permitting the blood level in the reservoir bag supported thereby to be visible from in front of or behind the reservoir mounting frame 80.

In all embodiments of the present invention, the mounting pins (both fixed and retractable) are preferably formed from stainless steel. The other structural components of the reservoir mounting bracket 20 (e.g., mount assembly 24, frame assembly 26 and oxygenator holder assembly 28) are preferably formed from aluminum.

The removable oxygenator holder assembly 28 is detachably mountable to the base member 40 of the mount assembly 24. A plurality of mounting apertures 118 are provided in the base member 40 (see FIGS. 4 and 5). Each mounting aperture 118 has an associated set screw 119 in the base member 40 to aid in securing the oxygenator holder assembly 28 in place on the base member 40.

The removable oxygenator holder assembly 28 has an oxygenator mounting post 120, an oxygenator support arm 122, an oxygenator holder frame 124, an indexing block 126 and an opposed cylindrical support 128. The oxygenator mounting post 120 is mountable in one of the plurality of oxygenator mounting apertures 118 of the base member 40 of the mount assembly 24. The alternative oxygenator mounting sites provided by the various mounting apertures 118 offer flexibility so that the reservoir mounting bracket 20 may support the oxygenator 30 in front, side or rear positions relative to the blood reservoir assembly. The post 120 has at least two annular grooves 121 therein which provide a seat for the set screw 119. Thus, the post 120 has two vertical positions relative to each mounting aperture 118, and can be rotated to any desired rotational orientation relative to such mounting aperture 118. The oxygenator support arm 122 extends from and is pivotally connected to the oxygenator mounting post 120, with its position fixed relative to the mounting post 120 by a thumb screw 129. The oxygenator may thus be oriented horizontally as seen in FIG. 1, or vertically (when the oxygenator holder assembly 28 is oriented as in FIGS. 2–7). The reservoir mounting bracket 20 thus supports both vertical and horizontal orientations of the oxygenator 30. The oxygenator holder frame 124 extends from the oxygenator support arm 122 and secures the oxygenator 30.

The oxygenator 30 (FIG. 1) is secured in the oxygenator holder assembly 28 by a spring plunger 132 and a pin 134. An end of the oxygenator 30 is placed in contact with and pushed against the spring plunger 132, compressing the spring plunger 132 inside the cylindrical support 128. While the spring plunger 132 is compressed, an outlet end 130 of the oxygenator 30 is mounted over the stationary indexing block 126. The pin 134, which is attached to the spring plunger 132, can then be moved into a locked position. Thus, the oxygenator 30 is secure and stable in the oxygenator holder assembly 28, as also illustrated in FIG. 1. The oxygenator 30 may be positioned to suit the blood circuit and perfision-management needs desired by the surgeon and dictated by oxygenator type and associated equipment.

Figure 9:
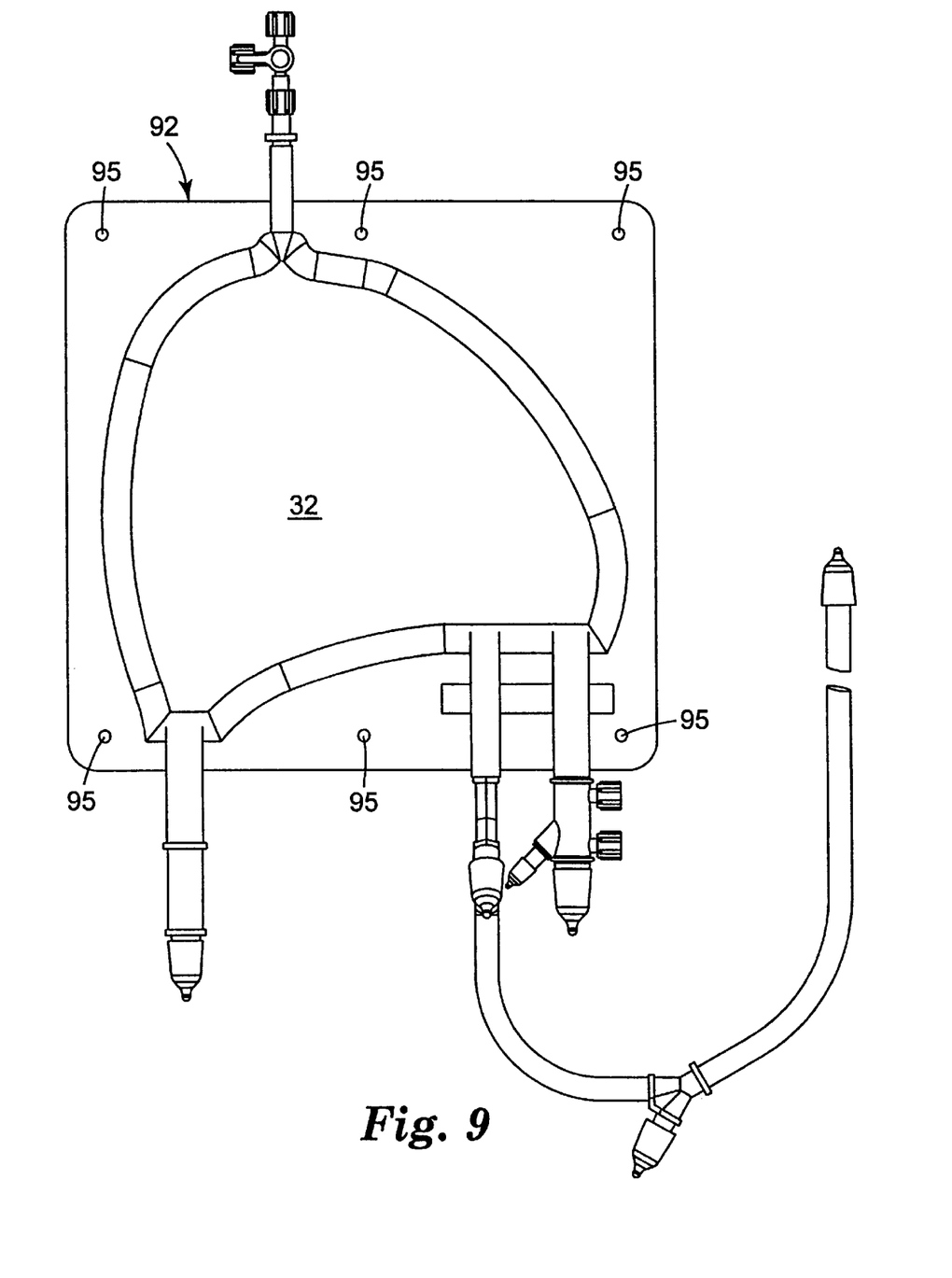
FIG. 9 is a front elevational view of a blood reservoir assembly adapted for use on the reservoir mounting bracket of the present invention.
Figure 10:
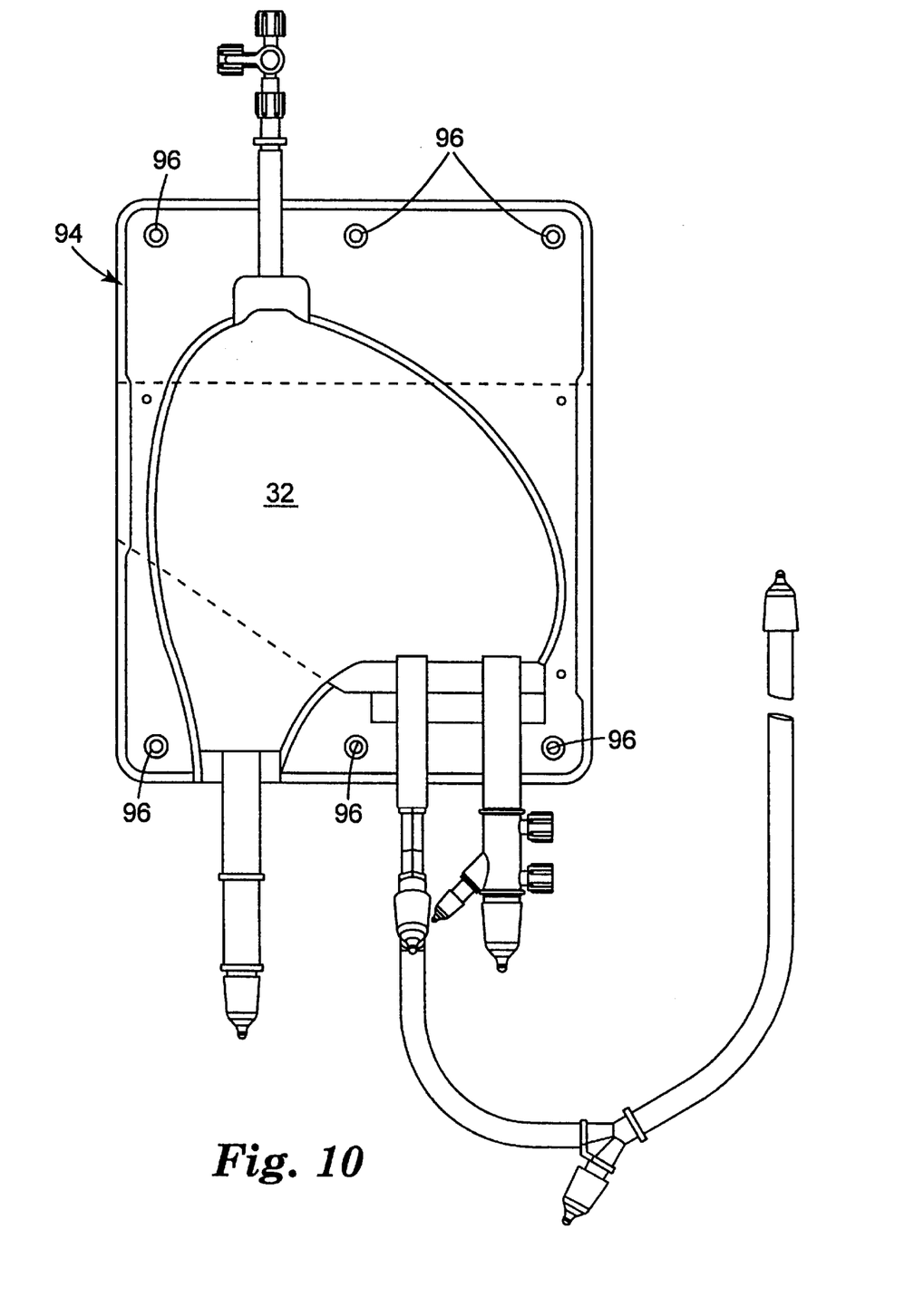
FIG. 10 is a front elevational view of a second, smaller blood reservoir assembly adapted for use on the reservoir mounting bracket of the present invention.

FIGS. 9 and 10 illustrate the blood reservoir assembly in greater detail. FIG. 9 shows the larger blood reservoir assembly 92, while FIG. 10 shows the smaller blood reservoir assembly 94. Both blood reservoir assemblies are composed of polyvinyl chloride reservoir bags and are flexible, sterile, nonpyrogenic and disposable. Each blood reservoir assembly is designed for a single use only, as reprocessing and resterilization after use may compromise its biocompatibility and functional integrity. In a preferred embodiment, the blood reservoir assembly 92 has a 1500 ml blood reservoir bag and the blood reservoir assembly 94 has a 750 ml blood reservoir bag.

The reservoir mounting bracket 20 also may accept a "hardshell" blood reservoir (not shown). In a hardshell arrangement, the frame assembly 26 would be replaced by the hardshell reservoir, which itself would have opposed side edges or tracks that would slide into the opposed channels 44 of the mounting assembly 24. Further, the oxygenator 30 can be attached directly to the hardshell blood reservoir, thereby eliminating the need for the oxygenator holder assembly 28. If the oxygenator 30 is not attached to the hardshell blood reservoir, the oxygenator holder assembly 28 attaches to the reservoir holder bracket 20 in the manner described above, and the oxygenator 30 is mounted thereon.

The reservoir mounting bracket of the present invention provides versatility and utility that has heretofore been unavailable. The mounting bracket is quite simple to use, and allows a user to mount a blood reservoir on a portion of the mounting bracket remote from the patient, and then quickly and easily mount that assembly on the mounting bracket itself for use. Further, the reservoir mounting bracket accepts multiple sizes of blood reservoir assemblies quite easily and without requiring special tools or fittings. The reservoir mounting bracket of the present invention supports both small and large volume flexible blood reservoirs, as well as hardshell blood reservoirs. The reservoir mounting bracket can be used as a stand-alone reservoir support, or with an oxygenator holder assembly affixed thereto, as required to meet space, convenience, or equipment dictated requirements. The reservoir mounting bracket of the present invention is designed for maximum flexibility in oxygenator support, so that the oxygenator can be arranged in front, side, rear, vertical or horizontal orientations. The reservoir mounting bracket of the present invention provides a highly efficient and effective means for allowing rapid adaptability and changeability of blood reservoir assemblies and related components in the surgical suite.

Although the present invention has been described with reference to preferred embodiments, workers skilled in the art will recognize that changes may be made in form and detail without departing from the spirit and scope of the invention.

What is claimed is:

1. A blood reservoir mounting bracket which is mountable on an upstanding pole, the mounting bracket comprising:

a substantially horizontal base member with two opposing end portions;

a pair of spaced apart frame supports which extend upwardly in a vertical orientation from said base member, one of said pair of frame supports being positioned on each said end portion of said base member;

wherein each frame support has a single receiving channel including an open side extending substantially the entire length of said frame support and wherein the open side of each said receiving channel faces the open side of the other receiving channel in an opposing orientation; and a reservoir mounting frame having a front surface and rear surface with opposite parallel side edges therebetween, the side edges of said reservoir mounting frame being slidably receivable with the facing open sides of said receiving channels of the frame supports to allow removable attachment of said reservoir mounting frame to said base member and frame supports.

2. The reservoir mounting bracket of claim 1, and further comprising:

means on the reservoir mounting frame for alternatively supporting either a first blood reservoir assembly or a second, larger blood reservoir assembly.

3. The reservoir mounting bracket of claim 2 wherein a first surface of said pair of frame supports define a reservoir presentation side of said mounting bracket, and wherein the reservoir mounting frame is movable between a first position adapted for supporting the first blood reservoir assembly when its front surface is facing the reservoir presentation side of the mounting bracket and a second position adapted for supporting the second, larger blood reservoir assembly when its rear surface is facing the reservoir presentation side of the mounting bracket.

4. The reservoir mounting bracket of claim 3 wherein each blood reservoir assembly has a plurality of mounting holes thereon, with the holes of the first reservoir assembly arrayed in a first pattern and the holes of the second reservoir assembly arrayed in a second, different pattern, and wherein the means for supporting comprises:

a first plurality of mounting pins on the front surface of the reservoir mounting frame which correspond to the pattern of mounting holes of the first reservoir assembly; and a second plurality of mounting pins on the rear surface of the reservoir mounting frame which correspond to the pattern of mounting holes on the second reservoir assembly.

5. The reservoir mounting bracket of claim 3 wherein each blood reservoir assembly has a plurality of mounting holes thereon, with the holes of the first reservoir assembly arrayed in a first pattern and the holes of the second reservoir assembly arrayed in a second, different pattern, and wherein the means for supporting comprises:

a plurality of retractable mounting pins disposed on the front surface of the reservoir mounting frame, with a first set of said pins being disposed to correspond to the first pattern of mounting holes on the first reservoir assembly and a second set of said pins being disposed to correspond to the second pattern of mounting holes on the second reservoir assembly.

6. The reservoir mounting bracket of claim 1, and further comprising:

an oxygenator holder assembly secured to the base member.

7. The reservoir mounting bracket of claim 6, wherein the oxygenator holder assembly comprises:

an oxygenator mounting post that attaches to the base member; and an oxygenator support arm extending from the mounting post.

8. The reservoir mounting bracket of claim 7 wherein the oxygenator mounting post is detachable from the base member and is attachable thereto at a plurality of mounting sites on the base member of the mount.

9. The reservoir mounting bracket of claim 8 wherein the oxygenator support arm is pivotally connected to the mounting post.

10. In a mounting bracket assembly for supporting a blood reservoir, said mounting bracket assembly comprising a substantially horizontal base member and a pair of spaced apart frame supports extending upwardly in a vertical orientation from said base member, and wherein said mounting bracket assembly includes a front reservoir presentation side and a back side defined by said pair of spaced apart frame supports and said base member, the improvement comprising:

the mounting bracket assembly including a detachable reservoir mounting frame having a front surface and a rear surface;

the frame being mountable relative to the mounting bracket assembly in a first position defined by said front surface of said mounting frame and said front reservoir presentation side of said bracket assembly, for supporting a first blood reservoir in an operable location; and, the frame being mountable relative to the mounting bracket assembly in a second alternative position defined by said rear surface of said mounting frame and said front reservoir presentation side of said bracket assembly, for supporting a second larger blood reservoir in the same operable location.

11. The mounting bracket assembly of claim 10 wherein the detachable reservoir mounting frame has opposite parallel side edges interposed between the front and rear surfaces of the frame, and the side edges of the reservoir mounting frame being slidably receivable within the facing grooves of the frame supports on the mount to allow removable mounting of the frame on the mount.

12. The mounting bracket assembly of claim 11, and further comprising:

means on the reservoir mounting frame for alternatively supporting either a first blood reservoir or a second, larger blood reservoir.

13. The mounting bracket assembly of claim 12, wherein the mount has a reservoir presentation side, and wherein the detachable reservoir mounting frame is movable between a first position adapted for supporting the first blood reservoir assembly when its front surface is facing the reservoir presentation side of the mount and a second position adapted for supporting the second, larger blood reservoir assembly when its rear surface is facing the reservoir presentation side of the mount.

14. The mounting bracket assembly of claim 13 wherein each blood reservoir has a plurality of mounting holes thereon, with the holes of the first blood reservoir arrayed in a first pattern and the holes of the second blood reservoir arrayed in a second, different pattern, and wherein the means for supporting comprises:

a first plurality of mounting pins on the front surface of the reservoir mounting frame which correspond to the pattern of mounting holes of the first blood reservoir; and a second plurality of mounting pins on the rear surface of the reservoir mounting frame which correspond to the pattern of mounting holes on the second blood reservoir.

15. The mounting bracket assembly of claim 13 wherein each blood reservoir has a plurality of mounting holes thereon, with the holes of the first blood reservoir arrayed in a first pattern and the holes of the second blood reservoir arrayed in a second, different pattern, and wherein the means for supporting comprises:

a plurality of retractable mounting pins disposed on the front surface of the reservoir mounting frame, with a first set of said pins being disposed to correspond to the first pattern of mounting holes on the first blood reservoir and a second set of said pins being disposed to correspond to the second pattern of mounting holes on the second blood reservoir.

16. The mounting bracket assembly of claim 10, and further comprising:

an oxygenator holder assembly secured to the mounting bracket assembly.

17. The mounting bracket assembly of claim 16, wherein the oxygenator holder assembly comprises:

an oxygenator mounting post that attaches to the base member of the mount; and an oxygenator support arm extending from the mounting post.

18. The mounting bracket assembly of claim 17 wherein the oxygenator mounting post is detachable from the base member of the mount and is attachable thereto at a plurality of mounting sites on the base member of the mount.

19. The mounting bracket assembly of claim 18 wherein the oxygenator support arm is pivotally connected to the mounting post.

* * * * *